United States Patent
Sebti et al.

(10) Patent No.: US 6,531,645 B1
(45) Date of Patent: Mar. 11, 2003

(54) RAS/P21 TRANSGENIC MOUSE

(75) Inventors: Said M. Sebti, Tampa, FL (US); Jalila Adnane, Tampa, FL (US); Warren J. Pledger, Tampa, FL (US); Rosalind Jackson, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/707,938

(22) Filed: Nov. 8, 2000

(51) Int. Cl.$^7$ .................... G01N 33/00; A01K 67/00; A01K 67/027
(52) U.S. Cl. .................... 800/3; 80/10; 80/18
(58) Field of Search ................ 800/3, 10, 18

(56) References Cited

PUBLICATIONS

Dexter et al., Chemotherapy of mammary carcinomas arising in ras transgenic mice, 1993, Investigational New Drugs, vol. 11, pp. 161–168.*
Weinberg et al., Loss of p21 CIP1/WAF1 does not recapitulate accelerated malignant conversion caused by p53 loss in experimental skin carcinogenesis, 1997, Oncogene, vol. 15, pp. 1685–1690.*
Topley et al., p21 WAF1/Cip1 functions as a suppressor of malignant skin tumor formation and a determination of keratinocyte stem–cell potential, 1999, Proc. Natl. Acad. Sci. USA, vol. 96, pp. 9089–9094.*
Sinn et al., Coexpression of MMTV/v–Ha–ras and MMTV/c–myc genes in transgenic mice: Synergistic action of oncogenes in vivo, 1987, Cell, vol. 49, pp. 465–474.*
Jackson et al., Tumor growth in P21 knockout X ras transgenic mice, 2000, Proceedings of the American Association for Cancer Research, vol. 41, pp. 575.*
Campbell et al., Totipotency or multipotentiality of cultured cells: applications and progtress, 1997, Theriogenology, vol. 47, pp. 63–72.*
Wall, Transgenic livestock: Progress and prospects for the future, 1996, Theriogenology, vol. 45, pp. 57–68.*
Sigmund et al., Viewpoint: Are studies in genetically altered mice out of control, 2000, Thromb. Vasc. Biol., vol. 20, pp. 1425–1429.*
Harvey et al., Genetic background alters the spectrum of tumors that develop in p53–deficient mice, 1993, Faseb, vol. 7, pp. 938–943.*

* cited by examiner

*Primary Examiner*—Remy Yucel
*Assistant Examiner*—Celine Qian
(74) *Attorney, Agent, or Firm*—Saliwanchik, Lloyd & Saliwanchik

(57) ABSTRACT

A transgenic rodent that constitutively expresses a ras protein in at least one tissue, is p21 null in at least one chromosome, and exhibits enhanced and accelerated ras-dependent tumorigenesis, together with methods for using said rodent, or cells derived thereof, for screening compounds or treatments for antitumor activity. In preferred embodiments, the rodent is a transgenic mouse that expresses a human ras oncogene operably linked to human regulatory sequences, and the cells of the mouse have at least one copy of a p21$^{WAF1/CIP1}$ transgene, whereby the mouse constitutively expresses a ras oncogene, and has decreased expression of p21. The rodents of the invention are useful in the study of ras-dependent oncogenesis and in the developments of treatments thereto.

13 Claims, 7 Drawing Sheets

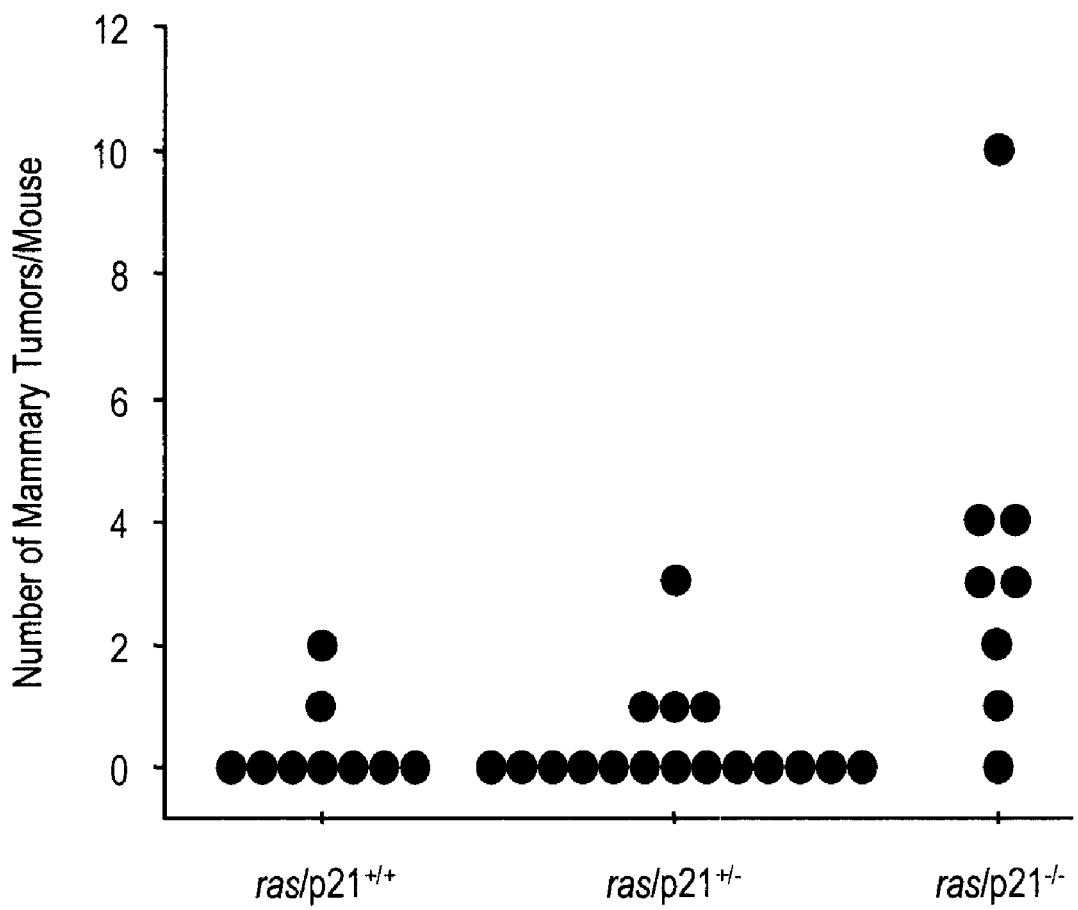

RAS/P21 TRANSGENIC MOUSE

SUPPORT

This work was supported by National Institutes of Health, National Cancer Institute Grants CA67771, CA72694, and CA78038. The Government may therefore have certain rights in the invention.

FIELD OF THE INVENTION

The present invention relates to the production and use of transgenic animal models and includes methods of modulating p21 phenotypes in a ras oncogene background. More particularly, the invention relates to the production and use of transgenic animals having decreased or null p21 expression in combination with constitutively activated ras expression, which are characterized by early and frequent tumorigenesis, and which provide improved models for the study of tumorigenesis and screening of anti-cancer agents and treatments.

BACKGROUND OF THE INVENTION

The ras oncogenes are frequently activated by point mutations or overexpression in human tumors. About 30% of all human tumors are associated with ras mutations and up to 95% of human pancreatic cancers contain K-ras mutations (Barbacid, 1990; Bos, 1989). Ras proteins are believed to mediate their oncogenic effect, in part, by dysregulating the cell cycle machinery (Downward, 1997; Ewen, 2000; Kerkhoff & Rapp, 1998). For instance, activated Ras, acting through the Raf/Mek/Erk kinase pathway, increases cyclin D1 expression and shortens the G1 phase of the cell cycle (Hitomi & Stacey, 1999; Liu et al., 1995). Moreover, Raf kinase was shown to interact with and regulate the activity of cdc25A, a phosphatase involved in the regulation of cdc2, an essential G2/M kinase (Xia et al., 1999). Unlike NIH3T3 cells, which have lost cyclin dependent kinase inhibitors (CKI) such as p16 or p19, activated Ras alone does not transform primary murine fibroblasts, but requires a cooperating oncogene (Franza et al., 1986; Hirakawa & Ruley, 1988; Parada et al., 1984; Yancopoulos et al., 1985). In fact, by itself, activated Ras causes growth arrest in these cells. From recent work, it is now apparent that this growth inhibitory effect of a strong Ras signal is due to the ability of the Raf/Mek/Erk pathway to induce expression of the CKI p21$^{WAF1/CIP1}$ (hereafter referred to as p21). A strong indication that the cell cycle arrest induced by a high intensity Ras/Raf signal is mediated by a high p21 level comes from the observation that in p21-deficient fibroblasts these signals do not lead to cell cycle arrest (Olson et al., 1998). These studies point to p21 as being one of the targets of the Ras/Raf signaling pathway. It is possible that the apparent ability of oncogenic Ras or Raf to induce the expression of p21 is a protective or stress response of the cell to receiving a strong Ras/Raf signal at an inappropriate stage in the cell cycle. p21 is induced in response to a broad spectrum of cellular stresses, thus allowing the cell to halt cell cycle progression. In normal human cells, p21 exists in a quaternary complex with a cyclin, a CDK, and the proliferating cell nuclear antigen (PCNA), a processivity factor of DNA polymerase δ (Zhang et al., 1993). p21 modulates CDK activity, thereby affecting cell cycle progression, whereas its effect on PCNA may be important in DNA replication and/or excision repair.

Investigation of naturally arising tumors has indicated that unlike p16, deletion or mutation of the p21 gene is not common in human tumors and is not a probable mechanism of inactivation of this gene (Balbin et al., 1996; Gao et al., 1995). The involvement of p21 in tumor suppression has also been questioned, as mice lacking p21 undergo a normal development, harbor no gross alterations in their organs, and exhibit no increase in spontaneous tumor development (Brugarolas et al., 1995; Deng et al., 1995). However, even in p53-deficient mice, spontaneous tumor formation occurred only in few tissues (Jacks et al., 1994). A similar study failed to show an effect of p21 on tumors formed by ras-transformed keratinocytes (Weinberg et al., 1997).

In the study of, and development of treatments for, ras-dependent tumors, there is a need for rapid means of screening possible compounds and treatments for efficacy. While it is desirable to use whole animals for this purpose to approximate at closely as possible the response of a patient and to enhance detection of toxicity, most mammalian tumor models suffer from a drawback in the length of time that is required to perform such a screening. Thus, suitable animals must be reared and allowed or induced to produce a suitable burden of tumors, which may take many months and is therefore costly in time and materials. Therefore, animal models in which the time required to produce a suitable tumor burden is shortened would be of great significance in accelerating the development of cancer treatments and the identification of new anti-cancer drugs or lead compounds.

In the present invention described herein, the aforementioned drawback is overcome by crossing p21-deficient mice with tumor-susceptible ras transgenic mice, wherein it is demonstrated by way of non-limiting example that p21-deficiency against a ras background dramatically accelerates the onset, and increases the multiplicity and aggressiveness, of Ras-dependent tumors.

DESCRIPTION OF THE FIGURES

Other advantages of the present invention will be readily appreciated as the same becomes better understood by reference to the following detailed description when considered in connection with the accompanying drawings wherein:

FIG. 3 shows tumor multiplicity in ras/p21$^{-/-}$, ras/p21$^{+/-}$ and ras/p21$^{+/+}$ mice. The number of mammary and salivary tumors developed in each ras/p21 group of mice by the age of 4 months is plotted. ras/p21$^{-/-}$ mice harbor 3.4 mammary tumors per mouse, while the ras/p21$^{+/-}$ and ras/p21$^{+/+}$ mice harbor an average of 0.35 and 0.33 mammary tumors per mouse.

BRIEF SUMMARY OF THE INVENTION

Figure 1A:
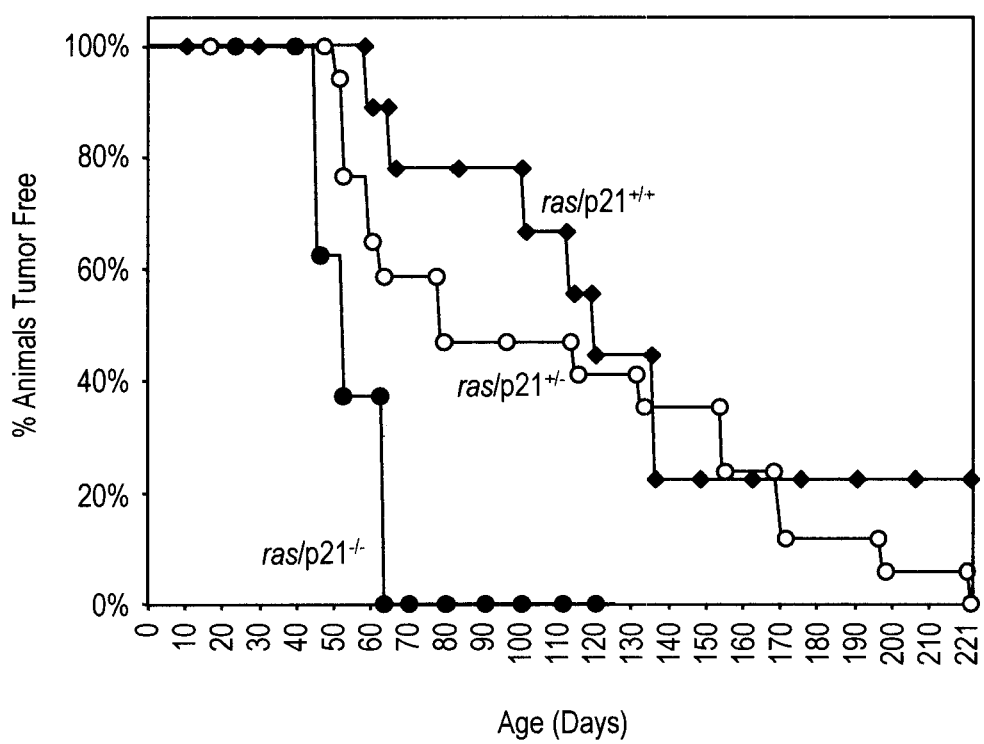
FIGS. 1A–D are figures showing tumor incidence in female MMTV/v-Ha-ras transgenic mice of different p21 genotypic backgrounds. Mice are monitored for tumors on a weekly basis by both observation and palpation. The age in days is recorded at the time of first observation of a tumor. The $T_{50}$ (age by which half of the mice develop tumors) for all tumors combined is 52 days for ras/p21$^{-/-}$ (n=8), 78 days for ras/p21$^{+/-}$ (n=17), and 120 days for ras/p21$^{+/+}$ (n=9) mice. Panel (A) shows the incidence of all tumors combined, (B) the incidence of Harderian gland hyperplasia, (C) the incidence of salivary tumors, and (D) the incidence of mammary tumors. The graphs represent actual tumor occurrence in the samples.

In its broadest aspect, the present invention provides improved means for screening anticancer treatments and anticancer compounds. Thus, rodents are provided that exhibit dramatically accelerated development of ras-dependent tumorigenesis, increased tumor burden, yet retain normal tumor development subsequent to the initial stages of tumorigenesis. By treating these animals with putative anticancer agents or treatments, a rapid answer can be obtained in vivo as to their efficaciousness. Alternatively, cells from such animals can be isolated, cultured, and contacted with compounds to be screened. Both embodiments significantly accelerate the rate at which new anticancer drugs and treatments can be evaluated.

Thus, in a first embodiment, the invention is a transgenic rodent that constitutively expresses a ras oncoprotein in at least one tissue, and is also p21-null in at least one chromosome, such that the expression of p21 protein is descreased compared to wild-type.

In preferred embodiments the rodent is a mouse and is homozygous in MMTV/v-Ha-ras. In most preferred embodiments, the mouse is homozygous null for p21$^{WAF1/CIP1}$.

In a second embodiment, the invention is a transgenic mouse which expresses a human ras oncogene operably linked to human regulatory sequences, where the mouse has at least one copy of a p21$^{WAF1/CIP1}$ transgene, and the mouse is characterized by constitutive expression of a ras oncogene, and decreased expression of p21.

In a third embodiment, the invention is a transgenic mouse whose genome has a first transgene comprising a DNA sequence encoding ras oncogene operably linked to a heterologous tissue-specific promoter, and in which the gene-product of the DNA sequence is expressed at elevated levels in at least some cells of a tissue, and the mouse has a second transgene comprising a DNA sequence encoding a p21-null mutant such that said mouse develops neoplasia or hyperplasia in said tissue.

In a fourth embodiment, the invention is a cell derived from the a tissue of the rodent of the present invention, which can be used, for example, for screening anticancer compounds.

Thus, in a fifth embodiment, the invention is a method for screening a compound for antitumor activity, in which the compound is administered to a transgenic rodent that constitutively expresses a ras protein in at least one tissue and is p21 null in at least one chromosome.

Finally, in a sixth embodiment, the invention is a method for screening a compound for antitumor activity, in which a cell isolated from one of the aforementioned transgenic rodents is contacted with a compound.

DETAILED DESCRIPTION OF THE INVENTION

The present invention provides transgenic animals with a modulated phenotype from that of the original/initial transgenic animals. The modulation is an enhancement of the original observed phenotype seen in the initial transgenic animals. By modulation is meant that the characteristic phenotype shown by the transgene is more pronounced, appears earlier or later; and where protein is produced more or less protein is produced than the parent strains or the like. Where earlier or accelerated, it is meant that the observed phenotype is seen at least one month earlier in the life-span than the phenotype in the parental strain or similarly for later appearance. For example, a modulated phenotype for a human disease model would show a pathology associated with the disease that more accurately reflects the human pathologic state including having more of the characteristics of the disease than the initial transgenic animal parental strains or the like. Alternatively, a modulated phenotype could reflect a faster or slower onset of the pathology of the human disease.

In general where the transgene carries a mutation it is referred to by the mutation. The mutation is abbreviated by the non-mutant amino acid followed by the location in the sequence followed by the substituted amino acid.

The offspring with the modulated phenotype are utilized in animal models as for example testing of treatment modalities in a disease model or for pathogen susceptibility. The transgenic parent can carry an overexpressed sequence, either the nonmutant or a mutant sequence and humanized or not as required. The term transgene is therefore used to refer to all these possibilities.

Additionally, cells can be isolated from the offspring which carry a transgene from each transgenic parent and that are used to establish primary cell cultures or cell lines as is known in the art.

Where appropriate, a parent strain will be homozygous for the transgene. Additionally, where appropriate, the endogenous nontransgene in the genome that is homologous to the transgene will be nonexpressive. By nonexpressive is meant that the endogenous gene will not be expressed and that this nonexpression is heritable in the offspring. For example, the endogenous homologous gene could be "knocked-out" by methods known in the art. Alternatively, the parental strain that receives one of the transgenes could carry a mutation at the endogenous homologous gene rendering it nonexpressed.

The transgenic parents are produced as is known in the art. The present invention provides for transgenic parental strains containing transgenes as described herein and including gene targeted or overexpressed mutant or nonmutant transgenes and where appropriate as well as for knockout strains carrying a transgene. Any method can be used which provides for stable, inheritable, expressible incorporation of the transgene within the nuclear DNA of an animal. These transgenic animals are constructed using standard methods known in the art and as set forth in U.S. Pat. Nos. 5,614,396 5,487,992, 5,464,764, 5,387,742, 5,347,075, 5,298,422, 5,288,846, 5,221,778, 5,175,384, 5,175,383, 4,873,191, 4,736,866 as well as Burke and Olson (1991), Capecchi (1989), Davies et al. (1992), Dickinson et al. (1993), Jakobovits et al. (1993), Lamb et al. (1993), Pearson and Choi (1993), Rothstein (1991), Schedl et al. (1993), Strauss et al. (1993). Further, patent applications WO 94/23049, WO 93/14200, WO 94/06908, WO 94/28123 also provide information.

More specifically, any techniques known in the art may be used to introduce the transgene expressibly into animals to produce the parental lines of animals. Such techniques include, but are not limited to, pronuclear microinjection (U.S. Pat. No. 4,873,191); retrovirus mediated gene transfer into germ lines (Van der Putten et al., 1985); gene targeting in embryonic stem cells (Thompson et al., 1989 and U.S. Pat. No. 5,614,396); electroporation of embryos (Lo, 1983); and spern-mediated gene transfer (Lavitrano et al., 1989). For a review of such techniques see Gordon (1989).

In an exemplar of the present invention as shown in the Example herein below a transgenic animal has been created for ras-dependent tumorigenesis, in one embodiment providing a model for tumorigensis of mammary tumors. The animal is a rodent and in a preferred embodiment, a mouse. As discussed herein above the pathology of ras-dependent tumorigenesis is accelerated by the absence of p21 expression in animals having constitutive ras expression. Therefore in this transgenic model, genes relating to ras and p21 have been used.

The above discussion provides a factual basis for developing transgenic animals which have a modified phenotype. The methods used with and the utility of the present invention can be shown by the following non-limiting examples and accompanying figures.

MATERIALS AND METHODS

Mice. Tumor-susceptible MTV/v-Ha-ras transgenic mice in an inbred FVB/N genetic background are used. $p21^{WAF1/CIP1}$ knockout mice ($p21^{-/-}$) of mixed 129/Sv and B6 background are likewise used. The generation, biological characterization, and tumor susceptibility of the MMTV/v-Ha-ras and $p_{21}^{WAF1/CIP1}$ knockout mice have been described previously (Brugarolas et al., 1995; Sinn et al., 1987), and the portions of these two references relating to preparation of MMTV/v-Ha-ras transgenic mice and $p21^{WAF1/CIP1}$ knockout mice, respectively, are herein specifically incorporated by reference. MMTV/v-Ha-ras transgenic mice are crossed with $p21^{WAF1/CIP1}$ knockout mice to generate three groups of mice carrying the v-Ha-ras transgene, but differing in their p21 dosage (ras/$p21^{-/-}$, ras/$p21^{+/-}$, ras/$p21^{+/+}$). Control mice of the same background differing in their p21 functional status ($p21^{+/+}$, $p21^{+/-}$, $p21^{-/-}$), but negative for the v-Ha-ras transgene, are also monitored.

Mouse Genotyping. The genotypes of four-week old offspring resulting from the crosses of the p21 knockout and MMTV/v-Ha-ras transgenic mice are determined by PCR. The PCR was performed using v-Ha-ras and p21 specific primers and genomic DNA isolated from a ~1 cm section of mouse tail by the method described in Davis et al. (Davis et al., 1980). For PCR, ~50 ng of DNA was amplified in the presence of 1.5 mM $MgCl_2$, 0.2 mM dNTP mix, 1× Qiagen buffer, 1 $\mu$M of each primer and 2 U of Taq polymerase (Qiagen). The sequence of the primers are the following:

R-MMTV/v-Ha-ras (GGGCATAAGCACAGATAAAACACT) (Seq. Id. No. 1)

F-MMTV/v-Ha-ras (CCCAAGGCTTAAGTAAGTTTTTGG) (Seq. Id. No. 2)

p21+116F (AAGC CTTGATTCTGATGTGGGC) (Seq. Id. No. 3)

p21–135 (TGACGAAGTCAAAGTTCCACCG) (Seq. Id. No. 4)

Neo–19+ (GCTATCAGGACATAGCGTTGGC) (Seq. Id. No. 5)

Sequences are given in a 5' to 3' direction.

Samples are incubated at 95° C. for 3 min before primer-specific cycling. Parameters are as follows: p21 (mutant= 750 bp, wt=900 bp) (95° C.–61° C.–72° C.)×40 cycles; v-Ha-Ras (852 bp) (95° C.–55° C.–72° C.)×30 cycles.

Tumor Development Monitoring and Sample Collection. The female offspring are monitored weekly for tumors by observation and palpation. Tumor diameters are measured in three dimensions using calipers, and tumor volume is calculated as length x width x height. Samples of tumor and normal tissue are collected in 10% neutral buffered formalin for histopathologic analysis. All surgical and experimental procedures performed on the mice are in accordance the NIH guidelines outlined in the "Guide for Care and Use of Laboratory Animals" (NIH publication 85–23). Animals are autopsied immediately after sacrifice, and external as well as internal organs are grossly examined. Representative tissue samples are obtained from salivary glands, mammary glands, lungs, liver, kidneys, spleen, and Harderian (lacrimal) glands. For general microscopy, tissues are embedded in paraffin, and 3 $\mu$m-thick sections are cut and stained with hematoxylin and eosin. Tissues are also processed using either an avidin-biotin complex method or a labeled streptavidin-biotin method after antigen retrieval. Tissues are immunostained with goat polyclonal antibodies again CD3ε, 1:400 dilution (T cell marker), and CD20, 1:200 (B cell marker) (Santa Cruz Biotechnology, Santa Cruz, Calif.), factor VIII, 1:400 dilution (endothelial cell marker) (Dako, Carpinteria, Calif.) and Ki-67 clone B56, 1:400 dilution (cell proliferation marker) (PharMingen, San Diego, Calif.). Negative and positive controls include the omission of the primary antibody and normal or tumor tissues with known high marker expression. $p21^{WAF1/CIP1}$ expression is analyzed by immunohistochemistry with an anti-p21 antibody (sc-397-G, Santa Cruz Biotechnology).

Mitotic Figure. A determination of the number of mitotic figures in tumor samples is performed by counting the number of visible mitotic figures within cells in 10 random HPFs (×400). The total number of mitotic figures is determined for all 10 HPFs, as well as the percentage of tumor cells with visible mitotic figures within each field. All mitotic counts are performed blinded with respect to the p21 genotype.

Apoptosis Detection in Tumor Samples. In situ labeling of apoptosis-induced DNA strand breaks is carried out using the ApopTag™ Peroxidase In Situ Apoptosis detection kit (Intergen Company, Caschase, N.Y.). Samples are deparaffinized and treated with proteinase K (2 μg/ml) for 15 min. Samples are then rinsed and incubated with 50 μl of TUNEL reaction solution containing 0.3 units/μl TdT (terminal deoxynucleotide transferase), TdT buffer, 0.01 nmol/μl biotin 16 dUTP, and 0.05 mg/ml BSA. Samples are incubated with 50 μl of staining solution (5% nonfat milk, 4× SSC, 0.1% Triton-X-100, and 2.5 μg/ml streptavidin-FITC). The number of apoptotic cells, from normal and tumor tissues, is counted in 10 random HPFs.

Statistical Analysis. The three groups of mice are compared with respect to frequencies using Fisher's Exact Test. For quantitative variables, the comparisons are done using the Kruskal Wallis Test for more than two groups. These were followed by Wilcoxon Rank Sum Tests for pairs of groups. All p-values are computed by exact methods.

EXAMPLE 1

Preparation and Phenotype of a Ras/$p21^{WAF1/CIP1}$ Transgenic Mouse p21-deficiency Cooperates with v-Ha-Ras to Accelerate Tumor Onset. To show the utility of p21 deficiency in the context of Ras-mediated tumorigenesis, female mammary tumor susceptible MMTV/v-Ha-ras transgenic mice are crossed with male p21 knockout mice. The MMTV promoter sequence controls the expression of the fused v-Ha-Ras oncogene, which contains activating mutations in codons 12 (Gly to Arg) and 59 (Ala to Thr). The MMTV/v-Ha-ras mice are highly susceptible to proliferative disturbances of the manmmary, salivary, and lymphoid tissues (Sinn et al., 1987), while heterozygous and p21 knockout mice develop normally (Brugarolas et al., 1995; Deng et al., 1995). At the second generation, offspring of the various genotypes that harbored the ras transgene and different dosages of p21 in a Mendelian ratio (ras/$p21^{-/-}$ (8 mice), ras/$p21^{+/-}$ (17 mice) and ras/$p21^{+/+}$ (9 mice)) are obtained. Mice from the same genetic background harboring different dosages of p21, but lacking the ras transgene, are kept as controls. All mice are monitored weekly for tumors by palpation. Noncarrier ras control siblings (n=9) do not develop tumors during the observation period. Histologic examination of the salivary and mammary tumors consistently reveals the presence of adenocarcinomas of the salivary and mammary tissue. When tumors are detected, their diameters are measured in three dimensions and measured at 1-week intervals until sacrificing of an animal is warranted due to the animal's tumor burden.

To show that p21 functional status influences tumor onset, the ras/$p21^{-/-}$ group of mice is compared with that of the ras/$p21^{+/-}$ and the ras/$p21^{+/+}$ mice. First the data are analyzed in terms of all tumors combined: malignant (mammary or salivary adenocarcinomas) and benign (Harderian gland hyperplasia). All the ras/$p21^{-/-}$ mice (8/8) develop tumors within 63 days of age. Half of these mice (4/8) develop tumors by age 52 ($T_{50}$=52 days) (FIG. 1A). In contrast, the ras/$p21^{+/+}$ mice (n=9) develop tumors at a later age ($T_{50}$=120 days) (p=0.0004). However, compared with the ras/$p21^{-/-}$ and the ras/$p21^{+/+}$ mice, the ras/$p21^{+/-}$ mice (n=17) develop tumors at an intermediate age ($T_{50}$=78 days) (p=0.0218 and p=0.0977, respectively). Furthermore, by 221 days of age, 22% of the ras/$p21^{+/+}$ mice are still tumor free whereas none of the ras/$p21^{-/-}$ mice are tumor free by age 63 days (FIG. 1A).

Figure 1B:
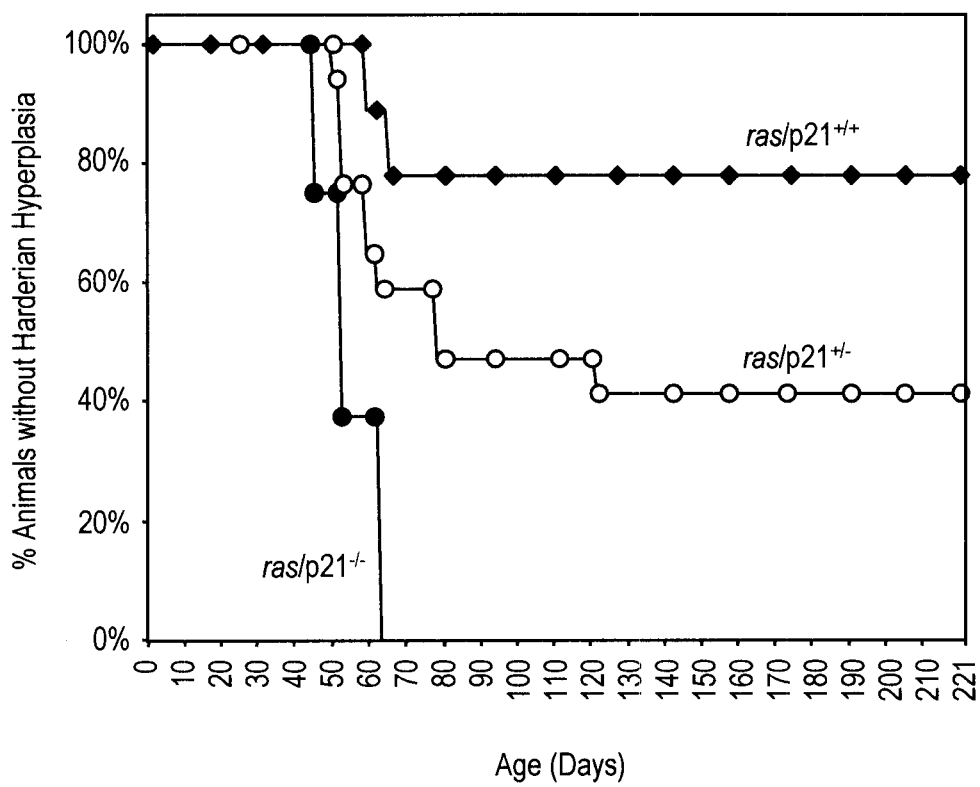
Figure 1C:
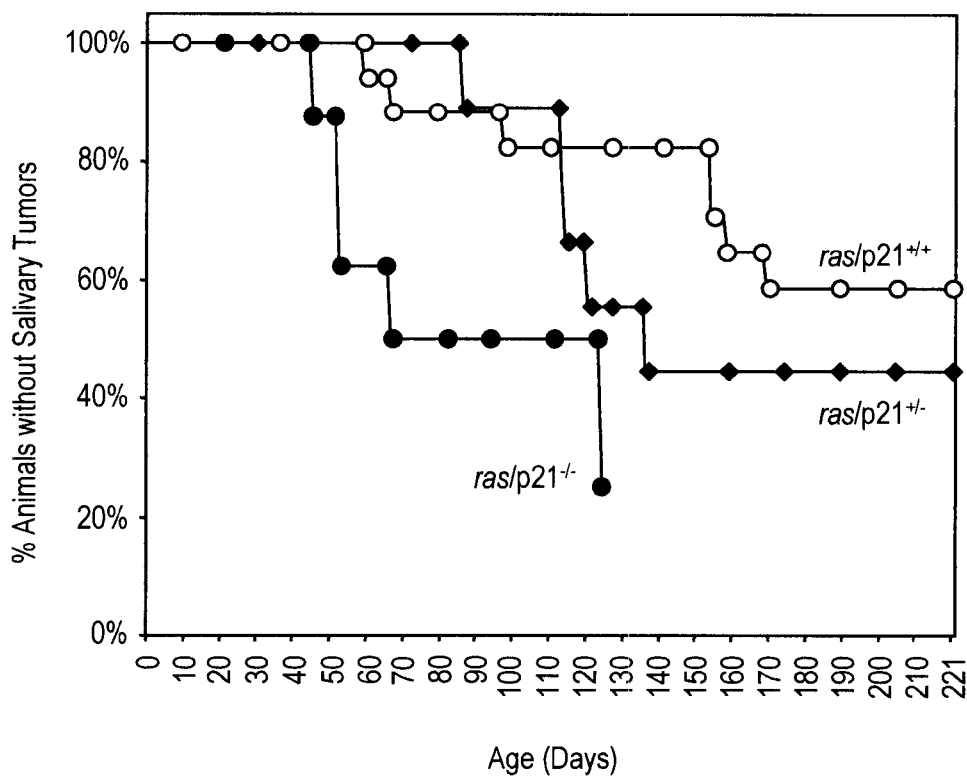
Figure 1D:
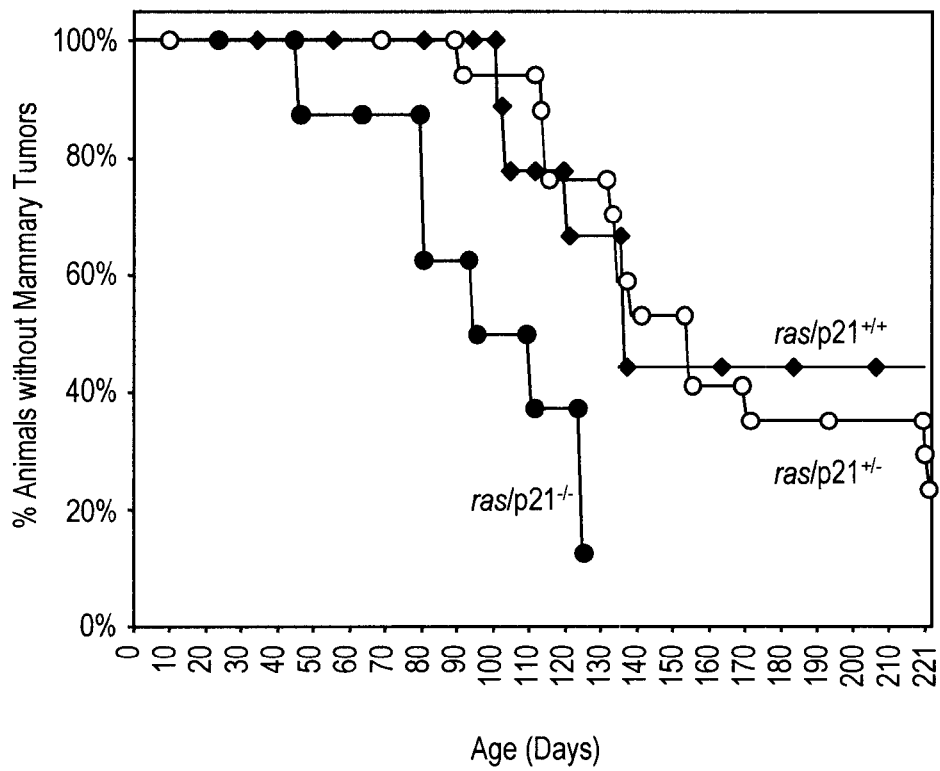

The effect of p21 loss on the onset of each tumor type separately is next shown. FIG. 1B shows that by 63 days of age, 100% of ras/$p21^{-/-}$ mice (n=8) have Harderian gland hyperplasia whereas, only 11% and 41% of ras/$p21^{+/+}$ (n=9) and ras/$p21^{+/-}$ (n=17) mice do, respectively. Thus, p21-deficiency enhances Harderian gland hyperplasia by 10-fold (p=0.0168 (+/−vs. −/−); p=0.0003 (+/+vs −/−); p=0.0509 (+/+vs +/−)). FIG. 1C shows that half of the ras/$p21^{-/-}$ mice develop salivary tumors by age 66 days, in contrast to ras/$p21^{+/+}$ and ras/$p21^{+/-}$ mice which have $T_{50}$ values of 136 and greater than 221 days of age, respectively (p=0.0001 (+/−vs. −/−); p=0.075 (+/+vs. −/−); p=0.3878 (+/+vs. +/−)). Similarly, FIG. 1D shows that the ras/$p21^{-/-}$ mice have a much shorter $T_{50}$ than the ras/$p21^{+/+}$ and the ras/$p21^{+/-}$ mice (94, 136 and 154 days, respectively) for mammary tumor development (p=0.0001(+/−vs −/−); p=0.0009(+/+VS −/−); p=0.5557(+/+vs +/−)).

Figure 4A:
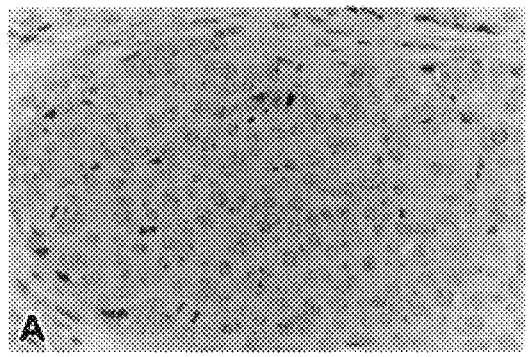
FIGS. 4A–F shows histopathology of tumors in ras/p21 mice. Mammary ductal carcinomas in ras/p21$^{-/-}$ (A) and ras/p21$^{+/+}$ (B) mice. Salivary gland acinic cell carcinomas in ras/p21$^{-/-}$ (C) and ras/p21$^{+/+}$ (D) mice. Note higher grade, slightly larger, and more hyperchromatic nuclei in tumors of ras/p21$^{-/-}$ animals (A and C). E-F, Low-power view (E) and Ki-67 immunostaining (F) of lung parenchyma with metastatic mammary ductal carcinoma. Tumor cells exhibit markedly higher proliferation, as shown by immunoreactive brown nuclei, than surrounding normal bronchial epithelium (F, arrow). A-D, ×500; E, ×50 (hematoxylin-eosin). F, ×500 (immunoperoxidase).
Figure 4B:
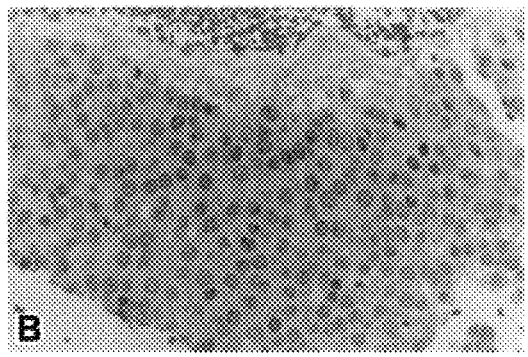
Figure 4C:
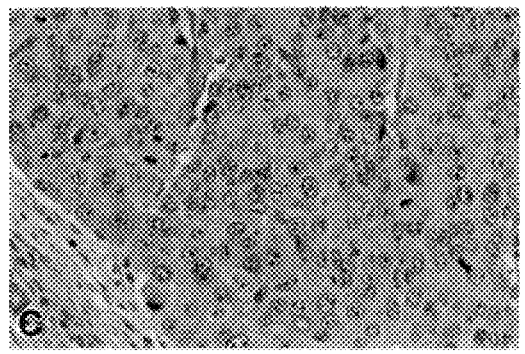
Figure 4D:
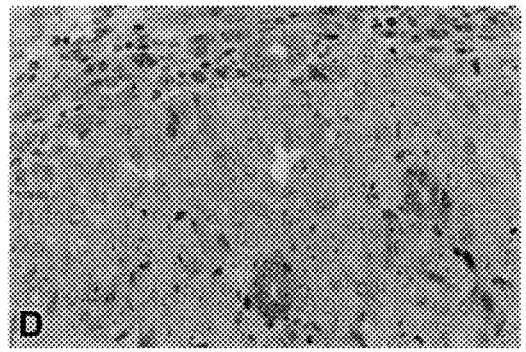
Figure 4E:
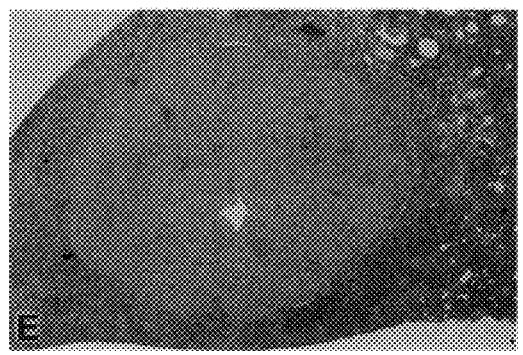

In the ras/$p21^{-/-}$ mice, salivary tumors appear first, followed by mammary tumors ($T_{50}$=66 days vs $T_{50}$=94 days) (Hazard Ratio=0.50, p=0.327). The hazard ratio is the ratio of the hazard of developing the first tumor to the hazard of developing the second at any time. For example, for the ras/$p21^{-/-}$ mice, the hazard ratio of 0.50 for mammary:salivary means that these mice have about 50% greater hazard of developing salivary tumors than mammary tumors. In contrast, in ras/$p21^{+/+}$ mice, the $T_{50}$=136 was the same for both mammary and salivary tumors. Moreover, a subcutaneous malignant vascular tumor of high grade, which expresses high levels of factor VIII, consistent with angiosarcoma, is identified in 1 out of 8 ras/$p21^{-/-}$ mice examined. Finally, at autopsy, 2 out of 8 ras/$p21^{-/-}$ mice and 1 out of 17 ras/$p21^{+/-}$ mice have metastatic mammary tumors visible on the surface of the lungs or in the abdomen (FIG. 4E). In contrast, none of the ras/$p21^{+/+}$ mice (n=9) develop tumor metastases (p=0.1932). Thus, tumor onset and incidence in MMTV/v-Ha-ras mice are p21-dependent with loss of p21 associated with an earlier tumor onset and increased tumor burden.

The most frequent abnormality detected is a bilateral hyperplasia of the Harderian lacrimal glands. By age 63 days, 8 out of 8 ras/$p21^{-/-}$ (100%), 7 out of 17 ras/$p21^{+/-}$ (41%) and 1 out of 9 ras/$p21^{+/+}$ (11%) mice have hyperplasia (−/−vs. +/+, p=0.0003; −/−vs. +/−, p=0.0168; +/−vs. +/+p=0.0509) (FIG. 1B). The Harderian gland is a tubulo-alveolar gland found within the orbit on the posterior aspect of the eyeball. Enlargement of the glands in ras/$p21^{-/-}$ mice is evident as early as 5 weeks after birth, with glands reaching up to 20 times their normal weight (average of 296.4±91.6 mg in hyperplastic glands vs. 18.4±1.5 mg in normal glands) by the age of 4 months. Histological examination of the tissue reveals a glandular hyperplasia with no evidence of focal or malignant tumors.

Figure 2A:
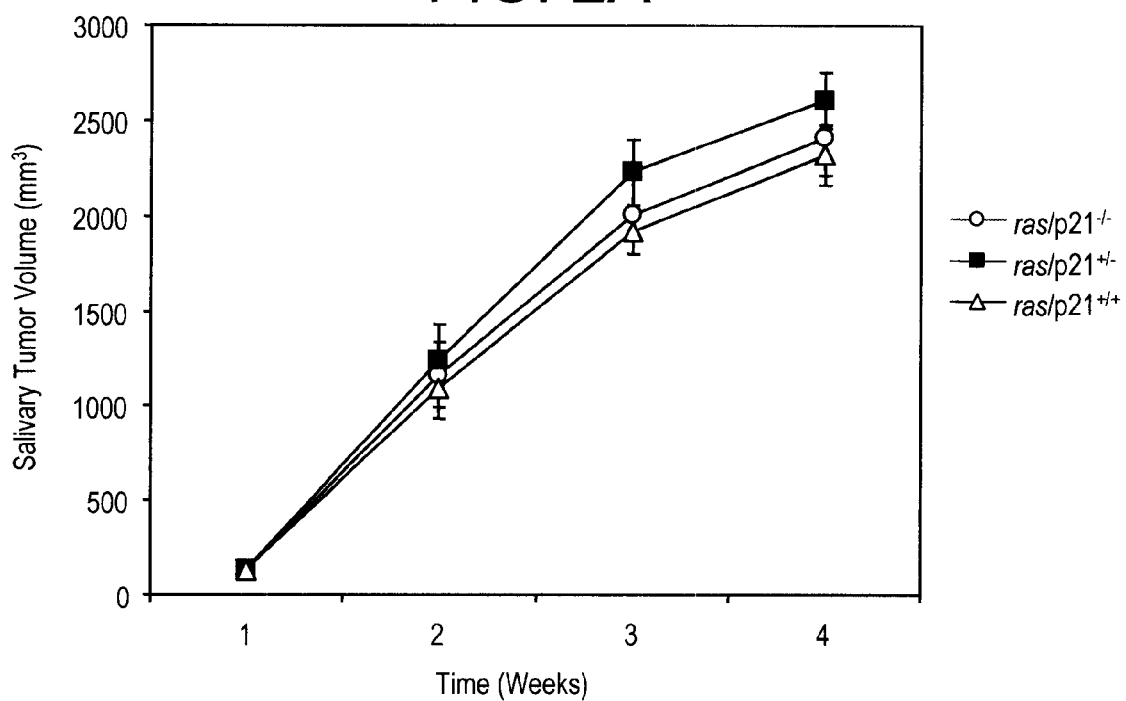
FIG. 2 shows salivary and mammary tumor growth rate in ras/p21$^{-/-}$, ras/p21$^{+/-}$ and ras/p21$^{+/+}$ mice. After the first observation of a mammary or salivary tumor, tumor size is measured weekly thereafter, and tumor volumes are calculated as previously described by Miller et al., 1988. The portions of Miller et al., 1988 that relate to tumor volume calculation are herein incorporated by reference. Time "1" represents the first day at which the tumor is observed, and Times "2" to "4" represent weekly subsequent measures of tumor volume. Average tumor volume for each genotype at weekly intervals is indicated. Bars representing SE determinations are indicated for mammary tumors (ras/p21$^{-/-}$ (n=6), ras/p21$^{+/-}$ (n=8), ras/p21$^{+/+}$ (n=5)) and salivary tumors (ras/p21$^{-/-}$ (n=5), ras/p21$^{+/-}$ (n=5), ras/p21$^{+/+}$ (n=5)).

Tumor Growth Rate and Multiplicity. The data described in FIG. 1 show that lack of p21 dramatically accelerates the onset of Ras-dependent tumorigenesis. To show that p21-deficiency does not affect the growth rate of tumors, the size of tumors was measured over time in the 3 different genetic backgrounds. The graphs in FIG. 2 show the tumor growth rate of salivary (panel A) and mammary (panel B) tumors for each group, ras/p21$^{-/-}$, ras/p21$^{+/-}$, and ras/p21$^{+/+}$ during a 4-week time period from the first day of tumor appearance. Although the salivary tumors of the ras/p21$^{-/-}$ mice grow at a somewhat faster rate than those of the ras/p21$^{+/+}$ mice, the difference is not statistically significant. A similar finding is obtained when the growth rate of mammary tumors of ras/p21$^{-/-}$ mice is compared with that of ras/p21$^{+/+}$ mice. Thus, the growth rate of the mammary and salivary tumors is independent of p21 functional status.

Figure 2B:
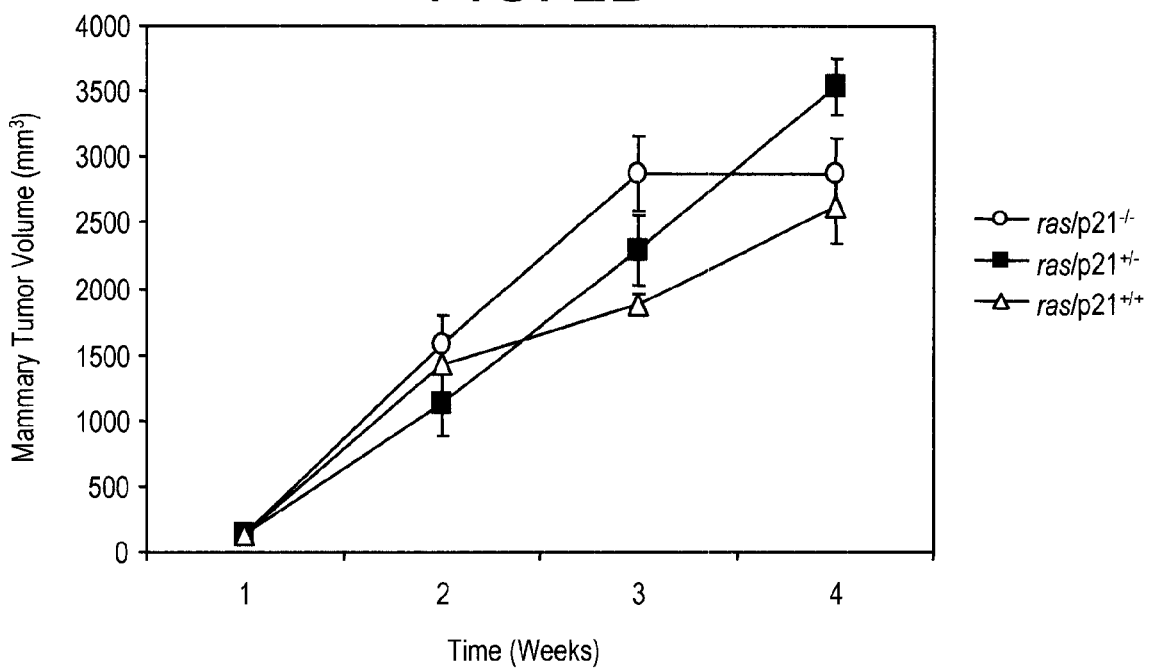

The effect of p21-deficiency in increasing the number of tumors developed per mouse (FIG. 3) is shown herein. Although tumor growth rate was not p21-dependent, the multiplicity of tumors was highly dependent on p21 dosage. FIG. 3 shows that, by the age of 115 days, the ras/p21$^{-/-}$ mice harbor multiple mammary tumors averaging 3.4 tumors per mouse. In contrast, the ras/p21$^{+/-}$ and ras/p21$^{+/+}$ mice harbor an average of 0.35 and 0.33 mammary tumors per mouse, respectively (p<0.0001 and p=0.0004) (FIG. 2B). Furthermore, at the time of sacrifice, the average of mammary tumors per mouse were 3.75, 2.11 and 1.33 for ras/p21−/−, ras/p21+/− and ras/p21+/+, respectively. Thus, although the tumor growth rate is independent of p21 functional status, the p21-deficient mice more frequently develop multiple tumors than do the p21-heterozygous or p21-wild type mice.

Figure 5A:
FIGS. 5A–H shows organ abnormality and histopathology of tumors in ras/p21 mice. (A) Gross morphology of spleen in ras/p21$^{-/-}$ (A, left) and ras/p21$^{+/+}$ (A, right) mice. The splenomegaly in ras/p21$^{-/-}$ animals is secondary to extramedullary hematopoiesis and to an atypical lymphoid proliferation, as shown by frequent megakaryocytes and enlarged lymphocytes (B). (C-D) The lymphoid population of ras/p21$^{-/-}$ animals contains frequent B cells and fewer T cells as indicated by immunoreactivity for CD20 (C) and CD3 (D), respectively. (E-F) immunostaining for p21 in mammary (E) and salivary gland (F) of ras/p21$^{+/+}$ mice. Note p21 expression in nuclei of benign stromal cells but not of tumor cells (E and F, arrow). (G) Negative immunostaining control in ras/p21$^{-/-}$ tumor tissue showing lack of immunodeposits in both stromal and tumor cells. (H) Subcutaneous soft tissue angiosarcoma in a ras/p21$^{-/-}$ animal exhibiting anastomosing microvascular channels lined by abnormal endothelial cells. (B and H). B×500 (hematoxylin-eosin). C-D, ×250 (ABC immunoperoxidase).
Figure 5B:
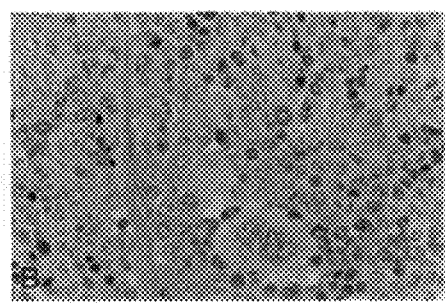
Figure 5C:
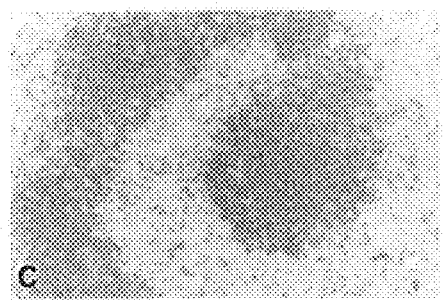
Figure 5D:
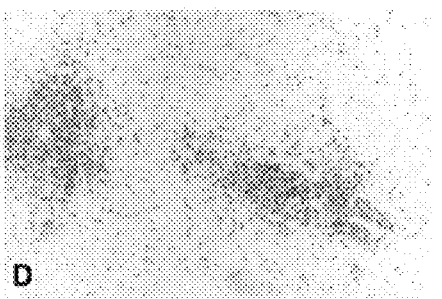
Figure 5E:
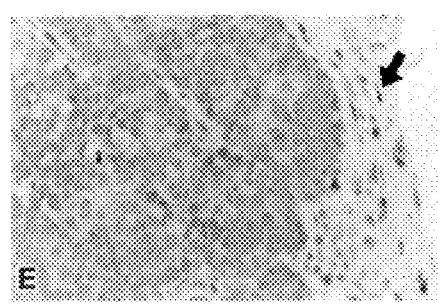
Figure 5F:
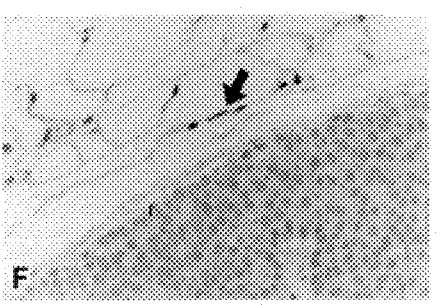
Figure 5G:
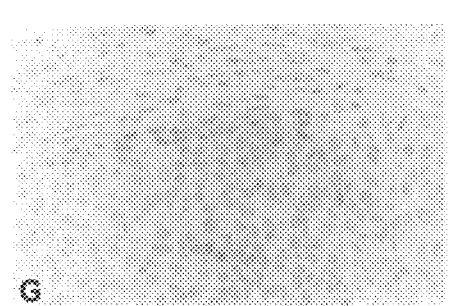
Figure 5H:
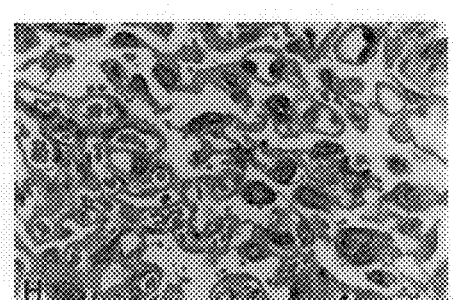
Figure 6:
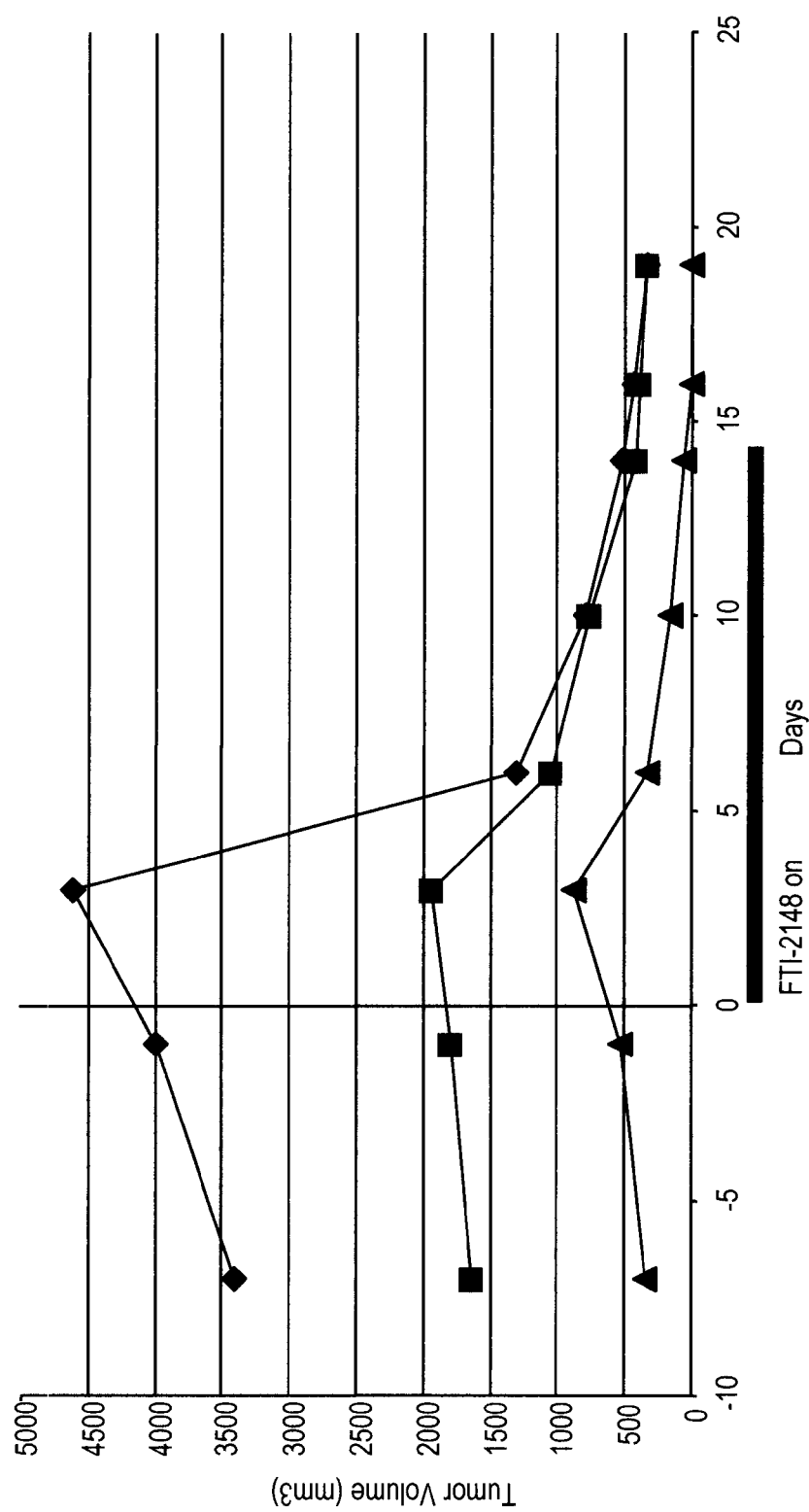
FIG. 6 shows the antitumor Efficacy of FTI-2148 in MMTV/v-Ha-ras/p21WAF1 (−/−) Transgenic Mice. The MMTV/v-Ha-Ras/p21waf(−/−) transgenic mice are generated as described herein. When the three mammary tumors reach 4500 mm$^3$, 2000 mm$^3$ and 900 mm$^3$ (see FIG. 1), the mice are implanted subcutaneously with an osmotic minipump that delivers 50 mg/Kg/day of the farnesyltransferase inhibitor FTI-2148 that was designed to block oncogenic H-Ras malignant transformation. This Figure shows that within 6 days of FTI-2148 treatment the tumors start to regress. By day 15, one tumor disappears whereas the two that started out at 4500 mm$^3$ and 2000 mm$^3$ regress to less than 500 mm$^3$. These studies clearly demonstrate the feasibility and practicality of using the novel mouse that is the subject of the present invention as a model in vivo to identify anticancer drugs. Thus, within 6 days of drug treatment one skilled in the art can determine whether a drug has antitumor activity.

Histopathology. The tumors, across the three genotypes, have a disorganized appearance with densely packed neoplastic cells with high mitotic and proliferation indices (FIG. 4A–D). Little or no normal tissue remains and areas of necrosis are common. There is a moderate inflammatory response in all of the mice, as evidenced by lymphocytic infiltration of tumor tissues. Moreover, ras/p21$^{-/-}$ and ras/p21$^{+/-}$ mice develop mammary adenocarcinomas of ductal type with higher nuclear grade than ras/p21$^{+/+}$ mice (FIG. 4A & B). The mice, across the three genotypes, develop adenocarcinomas of the salivary gland of acinar type (FIG. 4C & D). Furthermore, ras/p21$^{-/-}$ mice developed splenomegaly (FIG. 5A). The spleens from ras/p21$^{-/-}$ had average lengths of 3.3±0.7 cm, whereas ras/p21$^{+/+}$ had an average of 1.5±0.3 cm. Histologically, the splenomegaly is due to a moderate to marked extramedullary hematopoiesis, frequently displaying atypical lymphoid cells and megakariocytes (FIG. 5B). In the spleen, the labeling index with Ki-67 is 2.5 fold higher in ras/p21$^{-/-}$ than in ras/p21$^{+/+}$ mice (average of 55.6±10.2% vs. 21.1±7.7%). However, the overall level of apoptotic cells in the spleen is similar across the three genotypes. Thus, the lack of p21-induced enlargement of the spleen is principally due to an increase in cell proliferation rather than to a decrease in apoptosis. Representative tissue sections of spleen are stained with antibodies to CD3 and CD20 to characterize the type of proliferating cells present. A higher number of B cells and a smaller T-cell population are found, shwoing a polyclonal cell proliferation (FIG. 5C & 5D).

Tumor Growth Characteristics of MMTV/v-Ha-ras Mice Deficient in p21. Tumor growth reflects a balance between cell proliferation and cell death. The dynamics of this balance are herein shown in tumors from each genotypic group. In situ labeling of apoptotic cells is accomplished by the TUNEL method and positively stained cells are evaluated by light microscopy, as described in Materials and Methods. In both the ras/p21$^{+/+}$ and ras/p21$^{-/-}$ groups of mice, apoptosis is inhibited in salivary tumor samples by 10- and 12-fold, respectively (1.1±0.3% and 1.4±0.7% apoptotic cells, respectively) compared with normal salivary gland from non-carrier Ras control mice (13.7% apoptotic cells). Similar results are obtained with mammary tissue (normal mammary pads (18.4%), ras/p21$^{+/+}$ (1.6±0.9%) and ras/p21$^{-/-}$ (1.5±0.8%). Loss of p21 does not alter the apoptotic characteristics of the Ras-mediated salivary tumors.

Figure 4F:
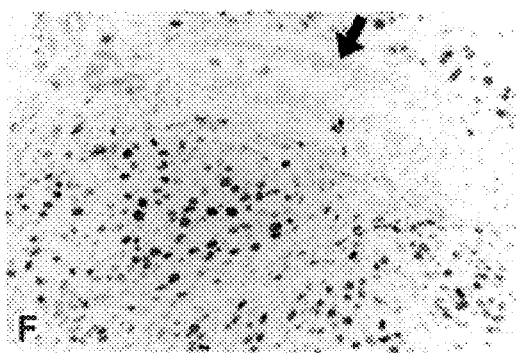

Two assays were used to assess tumor cell proliferation: mitotic figure counts and Ki-67 staining. The mitotic figure assay provides an estimate of the percentage of cells in a tumor undergoing division at one particular time. Mitotic figure counts are performed on H&E-stained tumor sections as described in Materials and Methods. The ras/p21$^{-/-}$ mammary tumor cells have an average of 65.3±10.4 mitotic figures, compared with 55.4±9.7 for the ras/p21$^{+/-}$ and 62.5±20.8 for the ras/p21$^{+/+}$ tumor cells. Similarly, the immunohistochemistry results with an anti-Ki-67 antibody show no significant difference in the Ki-67 level among the tumors across the three genotypes. High proliferation indices are found in all tumors, both within the primary tumors and the metastatic foci (FIG. 4F). p21 Expression is Decreased in Advanced ras/p21$^{+/+}$ Tumors. To show the status of p21 expression in tumors developed by ras/p21$^{+/+}$ mice, the paraffin-embedded tumor tissue is analyzed by immunohistochemistry with an anti-p21 antibody. In tumor tissue from two ras/p21$^{+/+}$ mice, p21 expression is absent in the nuclei of tumor cells, but present in the nuclei of adjacent stromal tissue (data not shown). However, p21 expression is unaltered in normal spleen and lung tissue collected from the same ras/p21$^{+/+}$ mice.

The induction of p21 by activated Ras represents a mechanism by which a cell facing a permanent active Ras signal avoids initiation of oncogenesis. The present invention is premised upon the fact that in the absence of p21, activated Ras signaling has no effective downstream block and tumor initiation and/or progression are augmented. In the present preferred embodiment, a mouse is prepared by transgenic techniques that, in contrast with the xenograft approach, permits the discrimination of tumor multiplicity and preserves stromal influences in the tumor's own microenvironment.

MMTV/v-Ha-ras transgenic mice are crossed into a p21-deficient background to show the in vivo function of p21 in the context of Ras oncogenesis. The long terminal repeat (LTR) of the mouse mammary tumor virus (MMTV) is used to direct expression of a number of oncogenes and growth factors to the mammary and salivary glands, with consequences ranging from mild hyperplasia to frank adenocarcinoma (Bouchard et al., 1989; Chooi et al., 1994; Daphna-lken et al., 1998; Iwamoto et al., 1990; Matsui et al., 1990; Ritland et al., 1997; Sinn et al., 1987; Wang et al., 1994; Yao et al., 1999). The ras transgenic models have demonstrated that mutation of ras genes can be an important factor in oncogenesis, but Ras oncoprotein, by itself, is not generally sufficient to induce tumorigenesis. Activation of a second oncogene, c-myc or SV40-T antigen, accelerates the onset of transformation, but does not change the overall disease pattern. In this Example, the offspring of the various genotypes harboring the ras transgene with differing dosages of p21 (ras/p2$^{-/-}$, ras/p21$^{+/-}$, ras/p21$^{+/+}$) are monitored for tumor formation. p21-deficient mice, carrying the ras transgene, develop tumors in a shorter time ($T_{50}=52$ days) compared with the p21-heterozygous ($T_{50}=78$ days) and p21-wild type ($T_{50}=120$ days) mice. Moreover, by the age of 4 months, ras/p21$^{-/-}$ mice develop an average of 3.4 mammary tumors per mouse while ras/p21$^{+/-}$ and ras/p21$^{+/+}$ mice develop an average of only 0.35 and 0.33 mammary tumors per mouse. Thus, p21 deficiency increases tumor multiplicity by 10-fold. Thus, p21-deficiency accelerates the onset of ras tumors and increases the number of tumors developed per mouse, demonstrating that p21-deficiency substitutes for changes that accelerate Ras-induced tumorigenesis.

While ras/p21$^{+/+}$ mice develop mammary tumors or salivary tumors at a similar relatively late age ($T_{50}=136$), ras/p21$^{-/-}$ mice tend to develop salivary tumors first ($T_{50}=66$), followed by mammary tumors ($T_{50}=94$). The salivary gland may be more sensitive than the mammary gland to p21-deficiency. At autopsy, 2 out of 8 ras/p21$^{-/-}$ and 1 out of 17 ras/p21$^{+/-}$ mice have metastatic mammary tumors on the lungs or abdomen, while no tumor metastases are observed in ras/p21$^{+/+}$ mice.

The tumor growth rate of ras/p21$^{-/-}$ mice is not higher than that of ras/p21$^{+/+}$ mice, and cell death and proliferation levels are similar across the three genotypes. The enhanced tumor onset and lack of effect on tumor growth rate and apoptosis show that p21-deficiency is critical for early but not late events of oncogenesis.

To summarize, this Example shows that the onset and multiplicity of tumors are different, but the overall tumor growth rates are similar, across the three genotypes, showing that p21 suppresses early but not late events of oncogenesis. Therefore, the ras/p21 transgenic mouse is a useful and informative model for testing therapies directed against Ras-associated tumorigenesis. Specifically, the early onset of tumorigenesis in the ras/p21 transgenic mouse is helpful in the testing of therapies and compounds because it decreases the time necessary to perform such tests.

EXAMPLE 2

Antitumor Efficacy of FTI-2148 in MMTV/v-Ha-ras/p21WAF1

(-/-) Transgenic Mice.

In this Example the utility of a preferred embodiment of the invention is demonstrated by showing antitumor activity of FTI-2148, an antitumor drug of known potency, in MMTV/v-Ha-Ras/p21 waf(-/-) transgenic mice generated as described herein. When three mammary tumors reach 4500 mm$^3$, 2000 mm$^3$ and 900 mm$^3$ (see FIG. 1), the MMTV/v-Ha-Ras/p2lwaf(-/-) transgenic mice are implanted subcutaneously with an osmotic mini-pump that delivers 50 mg/Kg/day of the farnesyltransferase inhibitor FTI-2148 that was designed to block oncogenic H-Ras malignant transformation. This Example shows that within 6 days of FTI-2148 treatment the tumors start to regress. By day 15, one tumor disappears whereas the two that started out at 4500 mm$^3$ and 2000 mm$^3$ regress to less than 500 mm$^3$. This Example clearly demonstrates the feasibility, utility and enablement of using the novel mouse that is the subject of the present invention as a model in vivo to identify anticancer drugs. Thus, within 6 days of drug treatment one skilled in the art can determine whether a candidate drug has antitumor activity.

Several printed publications and patent documents have been referred to in the foregoing disclosure. Each is hereby incorporated in its entirety by reference.

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

What is claimed is:

1. A transgenic mouse whose genome comprises a Ras oncogene and at least one p21 null allele, wherein said transgenic mouse constitutively expresses a Ras protein in at least one tissue and exhibits accelerated development of a salivary, mammary, or lachrymal gland tumor.

2. The transgenic mouse of claim 1 whose genome comprises a transgene encoding v-Ha-ras operably linked to a MMTV promoter, wherein said mouse is homozygous for the transgene.

3. The mouse of claim 1 in which said mouse is homozygous null for p 21.

4. A transgenic mouse whose genome comprises a human Ras oncogene operably linked to human regulatory sequences, said mouse comprising at least one p21 null allele, wherein said mouse constitutively expresses said ras oncogene, exhibits decreased expression of p21 mRNA, and further exhibits accelerated development of salivary, mammary, or lachrymal gland tumor.

5. A transgenic mouse whose genome comprises a first transgene comprising DNA sequence encoding ras operably linked to a heterologous tissue-specific promoter, wherein the ras protein is expressed at an elevated level in at least some cells of a tissue, and a second transgene comprising a p21 null allele such that said mouse develops neoplasia or hyperplasia in said tissue.

6. The transgenic mouse according to claim 5, wherein said tissue specific promoter is a mouse mammary tumor virus-long terminal repeat (MMTV-LTR) promoter.

7. An isolated mouse cell comprising a transgene, wherein said transgene comprises a DNA sequence encoding ras operably linked to a heterologous tissue-specific promoter and further comprises a DNA sequence encoding a p21 knockout gene, wherein said cell is isolated from a mammary gland, a salivary gland, or a lachrymal gland.

8. The mouse cell of claim 7, in which said cell is a cell of a salivary tumor, a mammary tumor, or a tumor of a lachrymal gland.

9. A method for screening a compound for antitumor activity, comprising administering to a transgenic mouse said compound, in which said transgenic mouse constitutively expresses a Ras protein in at least one tissue and is p21 null in at least one allele, wherein said transgenic mouse exhibits accelerated development of salivary, mammary, or lachrymal gland tumor; and monitoring the antitumor activity of said compound.

10. The method of claim 9 in which said mouse is homozygous null for p21.

11. The method of claim 9 wherein said mouse comprises in its genome a transgene encoding v-Ha-ras operably linked to a MMTV promoter, wherein said mouse is homozygous for the transgene.

12. A method for screening a cancer treatment for antitumor activity, comprising administering to a transgenic mouse said cancer treatment, in which said transgenic mouse constitutively expresses a ras protein in at least one tissue and is p21 null in at least one allele, wherein said transgenic mouse exhibits accelerated development of salivary, mammary, or lachrymal gland tumor; and monitoring the antitumor activity of said treatment.

13. A method for screening a compound for antitumor activity, comprising contacting a cell isolated from the transgenic mouse of claim 1 with said compound, in which said transgenic mouse constitutively expresses a ras protein in at least one tissue and is p21 null in at least one allele, wherein said transgenic mouse exhibits accelerated development of salivary, mammary, or lachrymal gland tumor; and monitoring the antitumor activity of said compound.

* * * * *

UNITED STATES PATENT AND TRADEMARK OFFICE
CERTIFICATE OF CORRECTION

PATENT NO.    : 6,531,645 B1
DATED         : March 11, 2003
INVENTOR(S)   : Said M. Sebti et al.

It is certified that error appears in the above-identified patent and that said Letters Patent is hereby corrected as shown below:

Column 7,
Line 54, "manmmary" should read -- mammary --.

Signed and Sealed this

Sixteenth Day of September, 2003

JAMES E. ROGAN
*Director of the United States Patent and Trademark Office*

SEQUENCE LISTING

<160> NUMBER OF SEQ ID NOS: 5

<210> SEQ ID NO 1
<211> LENGTH: 24
<212> TYPE: DNA
<213> ORGANISM: Mouse

<400> SEQUENCE: 1
gggcataagc acagataaaa cact                                        24

<210> SEQ ID NO 2
<211> LENGTH: 24
<212> TYPE: DNA
<213> ORGANISM: Mouse

<400> SEQUENCE: 2
cccaaggctt aagtaagttt ttgg                                        24

<210> SEQ ID NO 3
<211> LENGTH: 22
<212> TYPE: DNA
<213> ORGANISM: Mouse

```
<400> SEQUENCE: 3
aagccttgat tctgatgtgg gc                                                  22

<210> SEQ ID NO 4
<211> LENGTH: 22
<212> TYPE: DNA
<213> ORGANISM: Mouse

<400> SEQUENCE: 4
tgacgaagtc aaagttccac cg                                                  22

<210> SEQ ID NO 5
<211> LENGTH: 22
<212> TYPE: DNA
<213> ORGANISM: Mouse

<400> SEQUENCE: 5
gctatcagga catagcgttg gc                                                  22
```